United States Patent
Ketz et al.

(10) Patent No.: US 10,716,514 B1
(45) Date of Patent: Jul. 21, 2020

(54) SYSTEM AND METHOD FOR OPTIMIZED INDEPENDENT COMPONENT SELECTION FOR AUTOMATED SIGNAL ARTIFACT REMOVAL TO GENERATE A CLEAN SIGNAL

(71) Applicant: HRL Laboratories, LLC, Malibu, CA (US)

(72) Inventors: Nicholas A. Ketz, Topanga, CA (US); Matthew E. Phillips, San Diego, CA (US); Praveen K. Pilly, West Hills, CA (US)

(73) Assignee: HRL Laboratories, LLC, Malibu, CA (US)

( * ) Notice: Subject to any disclaimer, the term of this patent is extended or adjusted under 35 U.S.C. 154(b) by 249 days.

(21) Appl. No.: 15/891,218

(22) Filed: Feb. 7, 2018

Related U.S. Application Data (60) Provisional application No. 62/483,929, filed on Apr. 10, 2017.

(51) Int. Cl.
*A61B 5/00* (2006.01)
*A61B 5/0476* (2006.01)

(52) U.S. Cl.
CPC .......... *A61B 5/7203* (2013.01); *A61B 5/0006* (2013.01); *A61B 5/0476* (2013.01); *A61B 5/7221* (2013.01); *A61B 5/7225* (2013.01)

(58) Field of Classification Search
CPC ... A61B 5/7203; A61B 5/0006; A61B 5/0402; A61B 5/0245; A61B 2018/00839; A61B 5/0476; A61B 5/7225; A61B 5/7221
See application file for complete search history.

(56) References Cited

U.S. PATENT DOCUMENTS

| | | | |
|---|---|---|---|
| 5,230,344 A | 7/1993 | Oozdamar et al. | |
| 7,286,871 B2 | 10/2007 | Cohen | |
| 8,478,389 B1 | 7/2013 | Brockway et al. | |
| 8,805,482 B2* | 8/2014 | Sitzman | A61B 5/04017 600/509 |
| 2004/0161121 A1* | 8/2004 | Chol | G10L 21/0208 381/92 |

(Continued)

OTHER PUBLICATIONS

Daly, I., M. Billinger, R. Scherer, and G. Müller-Putz. "On the Automated Removal of Artifacts Related to Head Movement From the EEG." IEEE Transactions on Neural Systems and Rehabilitation Engineering 21, No. 3 (May 2013): pp. 427-434.

(Continued)

*Primary Examiner* — Gregory J Toatley, Jr.
*Assistant Examiner* — Lynda Dinh
(74) *Attorney, Agent, or Firm* — Tope-McKay & Associates

(57) ABSTRACT

Described is a system for automated artifact removal to generate a clean signal. During operation, the system selects initial noise components from a multi-channel, pre-processed signal by performing independent component analysis decomposition on the pre-processed signal to separate and rank the independent components as noise components. A clean signal is then generated through optimized selection of the noise components based on a signal quality index in which the noise components are moved from the original pre-processed signal until a sufficient signal quality is received.

12 Claims, 6 Drawing Sheets

(56) References Cited

U.S. PATENT DOCUMENTS

2012/0277548 A1* 11/2012 Burton ................ A61B 5/7203
600/301
2015/0327813 A1* 11/2015 Fu ........................ A61B 5/0476
600/383

OTHER PUBLICATIONS

Daly, Ian & Pichiorri, Floriana & Faller, Josef & Kaiser, Vera & Kreilinger, Alex & Scherer, Reinhold & Müller-Putz, Gernot. (2012). What does clean EEG look like?. Conference proceedings : . . . Annual International Conference of the IEEE Engineering in Medicine and Biology Society. IEEE Engineering in Medicine and Biology Society. Conference. 2012. 3963-3966.

M. Chaumon, D. V. M. Bishop, and N. A. Busch, "A practical guide to the selection of independent components of the electroencephalogram for artifact correction," Journal of Neuroscience Methods, vol. 250, pp. 47-63, Jul. 2015.

* cited by examiner

| Issue | Solution |
|---|---|
| Blink Artifact | ICA rejection of symmetric frontal components |
| Eye Movement | ICA rejection of asymmetric frontal components |
| 60Hz Noise | FIR Notch Filter |
| Bad Channel | Automatic Channel rejection of spectrum Z score <2 |
| Sweat Artifact | Running average baseline subtraction |
| Head Movements | Daly et al. Accelerometer/ICA correlation subtraction |

FIG. 6

SYSTEM AND METHOD FOR OPTIMIZED INDEPENDENT COMPONENT SELECTION FOR AUTOMATED SIGNAL ARTIFACT REMOVAL TO GENERATE A CLEAN SIGNAL

CROSS-REFERENCE TO RELATED APPLICATIONS

This application is a non-provisional patent application of U.S. 62/483,929, filed on Apr. 10, 2017, the entirety of which is hereby incorporated by reference.

GOVERNMENT RIGHTS

This invention was made with Government support under Contract Number W911NF-16-C-0018, awarded by ARMY/DARPA. The government has certain rights in the invention.

BACKGROUND OF INVENTION

(1) Field of Invention

The present invention relates to an artifact removal system and, more specifically, to a system and method for automated signal artifact removal.

(2) Description of Related Art

Electroencephalography (EEG) is an electrophysiological monitoring method used to record electrical activity of the brain. A problem with existing EEG techniques is that they are prone to being corrupted by signals other than the desired brain or neural signals. Such non-neural signals are referred to as artifacts and can detrimentally impact the readings or other processes that are dependent upon the EEG signals. As a result, several researchers have attempted to develop a variety of artifact removal techniques or methods.

State-of-the-art artifact removal methods first characterize multi-sensor data using Independent Components Analysis (ICA). This produces a representation of the data that best characterizes the separable components; however it is unclear which of these components is characteristic of the signal of interest, and which are characteristic of the noise. Once the noise components are identified (usually through visual inspection or correlation with recordings of known nuisance signals) these components can be subtracted from the data, yielding a de-noised signal to be used in subsequent analysis. For example, such a process is described by M. Chaumon, D. V. M. Bishop, and N. A. Busch, in "A practical guide to the selection of independent components of the electroencephalogram for artifact correction," *Journal of Neuroscience Methods*, vol. 250, pp. 47-63, July 2015, which is incorporated by reference as though fully set forth herein.

By way of example, Daly et al. published "On the Automated Removal of Artifacts Related to Head Movement From the EEG." *IEEE Transactions on Neural Systems and Rehabilitation Engineering* 21, no. 3 (May 2013): 427-34, which is incorporated by reference as though fully set forth herein. While somewhat operable, a major disadvantage of their method is the need for a measurement of the nuisance signal (i.e., the accelerometer data) and the lack of online validation that the selected components increase signal quality.

In other work, U.S. Pat. No. 7,286,871, by Mark Cohen, describes a "Method and apparatus for reducing contamination of an electrical signal", which is incorporated by reference as though fully set forth herein. The method of Cohen uses a contamination signal to subtract from the raw signals to improve generalized signal. One major disadvantage is the assumption that the remaining (post-subtracted) signal is a high-quality signal.

Yet another example is the system and method described in U.S. Pat. No. 5,230,344, by Oozdamar and Delgado, entitled, "Evoked potential processing system with spectral averaging, adaptive averaging, two dimensional filters, electrode configuration and method therefor," which is incorporated by reference as though fully set forth herein. Their method uses evoked potential (EP) and spectral averaging based on post signal processing running signal-to-noise ratio that determines the number of adaptive filtering processes. This method is limited to EP measurements with low and representative noise components to the EP. If this assumption does not hold, their method fails to operate.

Another process for artifact removal was described in U.S. Pat. No. 8,478,389, by Brockway and Brockway, entitled, "System for processing physiological data," which is incorporated by reference as though fully set forth herein. Their method uses features points and an estimated signal-to-noise (SNR) ratio to determine the cardiac rhythms for an electrocardiogram (EKG). Notably, their method is specific to EKG signals and would not generalize to any time series.

Given the description above, it is clear that prior work on adaptive thresholds is domain, task (Oozdamar and Delgado), and sensor specific (Brockway and Brockway). Thus, a continuing need exists for a generic noise or artifact removal system that is domain, task, and sensor agnostic.

SUMMARY OF INVENTION

A system for automated artifact removal to generate a clean signal. In various embodiments, the system comprises one or more processors and a memory. The memory is a non-transitory computer-readable medium having executable instructions encoded thereon, such that upon execution of the instructions, the one or more processors perform several operations, such as selecting initial noise components from a multi-channel, pre-processed signal; and generating a clean signal through optimized selection of the noise components based on a signal quality index. The clean signal is then recorded on a memory. It should be noted that the memory on or in which the clean signal is recorded or stored can be the same or different memory device that includes the instructions for performing the operations herein.

In another aspect, selecting initial noise components further comprises operations of generating a plurality of independent components by performing independent component analysis decomposition on the pre-processed signal; obtaining baseline signal quality measurements of the independent components based on the signal quality index; ranking the independent components based on known nuisance signals, otherwise ranking the independent components in random order; and adding one or more independent components to a current noise components list according to the rankings derived from SQI changes upon removal.

In yet another aspect, generating the clean signal through optimized selection of the noise components further comprises operations of removing the independent components in the current noise components list from the pre-processed signal by removing each selected independent component from each channel in the multi-channel, pre-processed signal; evaluating a change in signal quality by comparing a current signal quality index with a baseline signal quality or a signal quality index from a previous iteration; if signal quality increases, adding a next highest ranking independent component to the noise components list; and if signal quality decreases, removing a lowest ranking independent component from the noise components list.

In another aspect, the process of generating the clean signal through optimized selection of the noise components is repeated until N components remain unselected or a change in signal quality is below a predetermined threshold.

Finally, the present invention also includes a computer program product and a computer implemented method. The computer program product includes computer-readable instructions stored on a non-transitory computer-readable medium that are executable by a computer having one or more processors, such that upon execution of the instructions, the one or more processors perform the operations listed herein. Alternatively, the computer implemented method includes an act of causing a computer to execute such instructions and perform the resulting operations.

BRIEF DESCRIPTION OF THE DRAWINGS

The objects, features and advantages of the present invention will be apparent from the following detailed descriptions of the various aspects of the invention in conjunction with reference to the following drawings, where.

DETAILED DESCRIPTION

The present invention relates to an artifact removal system and, more specifically, to a system and method for automated signal artifact removal. The following description is presented to enable one of ordinary skill in the art to make and use the invention and to incorporate it in the context of particular applications. Various modifications, as well as a variety of uses in different applications will be readily apparent to those skilled in the art, and the general principles defined herein may be applied to a wide range of aspects. Thus, the present invention is not intended to be limited to the aspects presented, but is to be accorded the widest scope consistent with the principles and novel features disclosed herein.

In the following detailed description, numerous specific details are set forth in order to provide a more thorough understanding of the present invention. However, it will be apparent to one skilled in the art that the present invention may be practiced without necessarily being limited to these specific details. In other instances, well-known structures and devices are shown in block diagram form, rather than in detail, in order to avoid obscuring the present invention.

The reader's attention is directed to all papers and documents which are filed concurrently with this specification and which are open to public inspection with this specification, and the contents of all such papers and documents are incorporated herein by reference. All the features disclosed in this specification, (including any accompanying claims, abstract, and drawings) may be replaced by alternative features serving the same, equivalent or similar purpose, unless expressly stated otherwise. Thus, unless expressly stated otherwise, each feature disclosed is one example only of a generic series of equivalent or similar features.

Furthermore, any element in a claim that does not explicitly state "means for" performing a specified function, or "step for" performing a specific function, is not to be interpreted as a "means" or "step" clause as specified in 35 U.S.C. Section 112, Paragraph 6. In particular, the use of "step of" or "act of" in the claims herein is not intended to invoke the provisions of 35 U.S.C. 112, Paragraph 6.

Before describing the invention in detail, first a description of the various principal aspects of the present invention is provided. Subsequently, an introduction provides the reader with a general understanding of the present invention. Finally, specific details of various embodiment of the present invention are provided to give an understanding of the specific aspects.

(1) Principal Aspects

Various embodiments of the invention include three "principal" aspects. The first is a system for optimized independent component selection for automated artifact removal. The system is typically in the form of a computer system operating software or in the form of a "hard-coded" instruction set. This system may be incorporated into a wide variety of devices that provide different functionalities. The second principal aspect is a method, typically in the form of software, operated using a data processing system (computer). The third principal aspect is a computer program product. The computer program product generally represents computer-readable instructions stored on a non-transitory computer-readable medium such as an optical storage device, e.g., a compact disc (CD) or digital versatile disc (DVD), or a magnetic storage device such as a floppy disk or magnetic tape. Other, non-limiting examples of computer-readable media include hard disks, solid state hard drives, read-only memory (ROM), and flash-type memories. These aspects will be described in more detail below.

Figure 1:
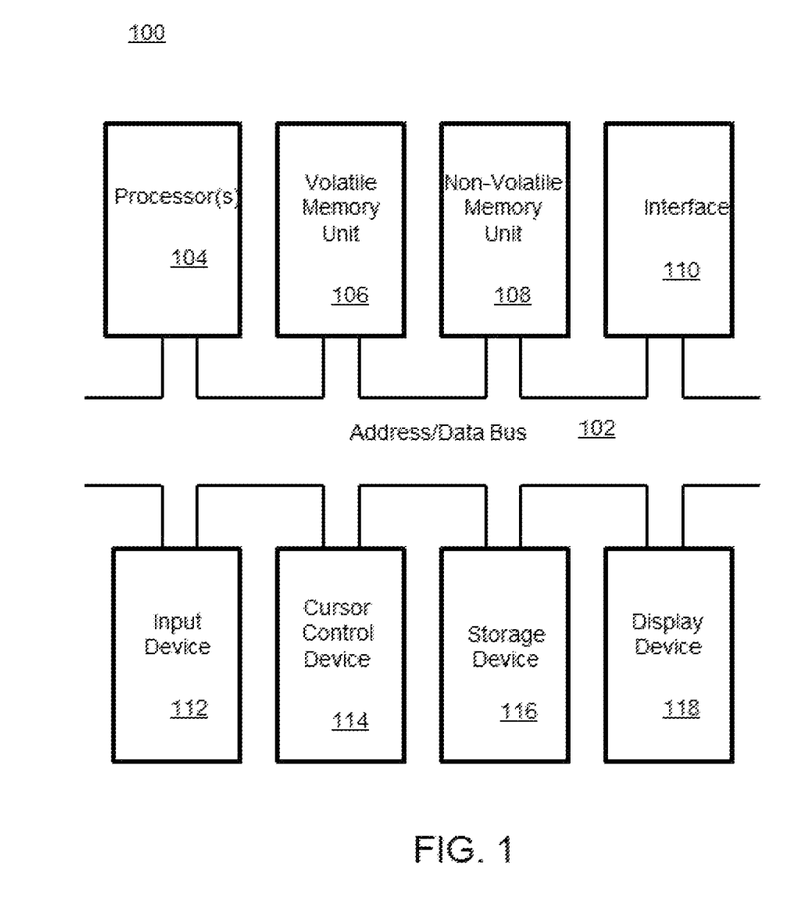
FIG. 1 is a block diagram depicting the components of a system according to various embodiments of the present invention.

A block diagram depicting an example of a system (i.e., computer system 100) of the present invention is provided in FIG. 1. The computer system 100 is configured to perform calculations, processes, operations, and/or functions associated with a program or algorithm. In one aspect, certain processes and steps discussed herein are realized as a series of instructions (e.g., software program) that reside within computer readable memory units and are executed by one or more processors of the computer system 100. When executed, the instructions cause the computer system 100 to perform specific actions and exhibit specific behavior, such as described herein.

The computer system 100 may include an address/data bus 102 that is configured to communicate information. Additionally, one or more data processing units, such as a processor 104 (or processors), are coupled with the address/data bus 102. The processor 104 is configured to process information and instructions. In an aspect, the processor 104 is a microprocessor. Alternatively, the processor 104 may be a different type of processor such as a parallel processor, application-specific integrated circuit (ASIC), programmable logic array (PLA), complex programmable logic device (CPLD), or a field programmable gate array (FPGA).

The computer system 100 is configured to utilize one or more data storage units. The computer system 100 may include a volatile memory unit 106 (e.g., random access memory ("RAM"), static RAM, dynamic RAM, etc.) coupled with the address/data bus 102, wherein a volatile memory unit 106 is configured to store information and instructions for the processor 104. The computer system 100 further may include a non-volatile memory unit 108 (e.g., read-only memory ("ROM"), programmable ROM ("PROM"), erasable programmable ROM ("EPROM"), electrically erasable programmable ROM "EEPROM"), flash memory, solid state hard drives, etc.) coupled with the address/data bus 102, wherein the non-volatile memory unit 108 is configured to store static information and instructions for the processor 104. Alternatively, the computer system 100 may execute instructions retrieved from an online data storage unit such as in "Cloud" computing. In an aspect, the computer system 100 also may include one or more interfaces, such as an interface 110, coupled with the address/data bus 102. The one or more interfaces are configured to enable the computer system 100 to interface with other electronic devices and computer systems. The communication interfaces implemented by the one or more interfaces may include wireline (e.g., serial cables, modems, network adaptors, etc.) and/or wireless (e.g., wireless modems, wireless network adaptors, etc.) communication technology.

In one aspect, the computer system 100 may include an input device 112 coupled with the address/data bus 102, wherein the input device 112 is configured to communicate information and command selections to the processor 100. In accordance with one aspect, the input device 112 is an alphanumeric input device, such as a keyboard, that may include alphanumeric and/or function keys. Alternatively, the input device 112 may be an input device other than an alphanumeric input device. In an aspect, the computer system 100 may include a cursor control device 114 coupled with the address/data bus 102, wherein the cursor control device 114 is configured to communicate user input information and/or command selections to the processor 100. In an aspect, the cursor control device 114 is implemented using a device such as a mouse, a track-ball, a track-pad, an optical tracking device, or a touch screen. The foregoing notwithstanding, in an aspect, the cursor control device 114 is directed and/or activated via input from the input device 112, such as in response to the use of special keys and key sequence commands associated with the input device 112. In an alternative aspect, the cursor control device 114 is configured to be directed or guided by voice commands.

In an aspect, the computer system 100 further may include one or more optional computer usable data storage devices, such as a storage device 116, coupled with the address/data bus 102. The storage device 116 is configured to store information and/or computer executable instructions. In one aspect, the storage device 116 is a storage device such as a magnetic or optical disk drive (e.g., hard disk drive ("HDD"), floppy diskette, compact disk read only memory ("CD-ROM"), digital versatile disk ("DVD")). Pursuant to one aspect, a display device 118 is coupled with the address/data bus 102, wherein the display device 118 is configured to display video and/or graphics. In an aspect, the display device 118 may include a cathode ray tube ("CRT"), liquid crystal display ("LCD"), field emission display ("FED"), plasma display, or any other display device suitable for displaying video and/or graphic images and alphanumeric characters recognizable to a user.

The computer system 100 presented herein is an example computing environment in accordance with an aspect. However, the non-limiting example of the computer system 100 is not strictly limited to being a computer system. For example, an aspect provides that the computer system 100 represents a type of data processing analysis that may be used in accordance with various aspects described herein. Moreover, other computing systems may also be implemented. Indeed, the spirit and scope of the present technology is not limited to any single data processing environment. Thus, in an aspect, one or more operations of various aspects of the present technology are controlled or implemented using computer-executable instructions, such as program modules, being executed by a computer. In one implementation, such program modules include routines, programs, objects, components and/or data structures that are configured to perform particular tasks or implement particular abstract data types. In addition, an aspect provides that one or more aspects of the present technology are implemented by utilizing one or more distributed computing environments, such as where tasks are performed by remote processing devices that are linked through a communications network, or such as where various program modules are located in both local and remote computer-storage media including memory-storage devices.

Figure 2:
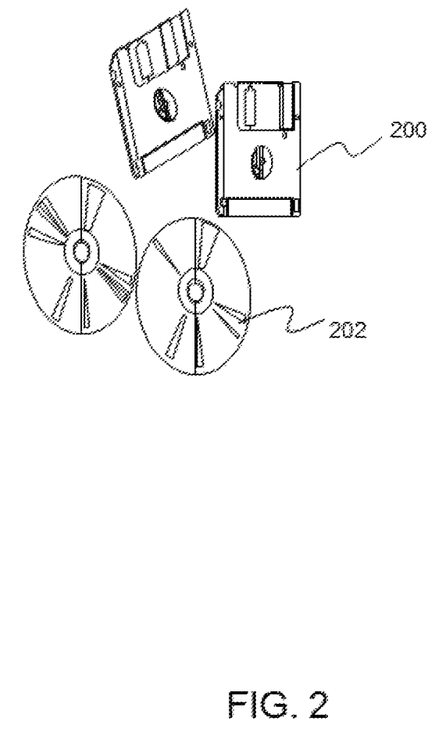
FIG. 2 is an illustration of a computer program product embodying an aspect of the present invention.

An illustrative diagram of a computer program product (i.e., storage device) embodying the present invention is depicted in FIG. 2. The computer program product is depicted as floppy disk 200 or an optical disk 202 such as a CD or DVD. However, as mentioned previously, the computer program product generally represents computer-readable instructions stored on any compatible non-transitory computer-readable medium. The term "instructions" as used with respect to this invention generally indicates a set of operations to be performed on a computer, and may represent pieces of a whole program or individual, separable, software modules. Non-limiting examples of "instruction" include computer program code (source or object code) and "hard-coded" electronics (i.e. computer operations coded into a computer chip). The "instruction" is stored on any non-transitory computer-readable medium, such as in the memory of a computer or on a floppy disk, a CD-ROM, and a flash drive. In either event, the instructions are encoded on a non-transitory computer-readable medium.

(2) Introduction

This disclosure is directed to an artifact removal system for removing artifacts or noisy signals from electroencephalography (EEG) and other suitable signal data and systems. State-of-the-art artifact removal methods first characterize multi-sensor data using Independent Components Analysis (ICA). This produces a representation of the data that best characterizes the separable components, however it is unclear which of these components is characteristic of the signal of interest, and which are characteristic of the noise. Once the noise components are identified (usually through visual inspection or correlation with recordings of known nuisance signals) these components can be subtracted from the data, yielding a de-noised signal to be used in subsequent analysis. However and as noted above, existing techniques fail to sufficiently distinguish the noise components.

The system of this disclosure dramatically improves the technology in EEG and signal processing. When implemented, the system automatically selects the noise components by assessing a measure of signal quality before and after subtracting any given component through rank-ordering these components and only removing the components that increase the signal quality. If the number of sensor channels in the data set are relatively small, all possible permutations can be tested, and the best possible combination of noise components can be selected and removed. If the number of channels is sufficiently large more sophisticated optimization methods can be used to guide the selection process, and stop once some criteria is reached. A unique aspect of the system is an optimization process used to select which components of a multi-channel sensor best characterize the 'noise' or undesired signals within the recorded data.

The invention of the present disclosure has been developed and tested in the measurement domain of human EEG in which currently there is no fully automated artifact rejection method. However, it should be understood that although this invention is described with respect to EEG, the disclosed method and system is not intended to be limited thereto as it allows for automated removal of noise from any multi-channel sensor array while ensuring that the signal quality will not degrade in the process, and allows for a standardization of artifact removal across data sets. For example, the system is currently implemented in Matlab with data from a 32 channel EEG system produced by NeuroElectrics providing the input data; however, it is directly applicable to any EEG system. More generally, this invention can be adapted to any multi-channel sensor system provided an independent measure of signal quality exists or can be developed. Further, this method can be applied to time-series data of any size or type, provided that there exists some independent measure of signal quality. A benefit of this invention is improved brain-machine-interface, potential disease diagnostic improvements in classification and detection performance, as well as a reduction in man hours required for cleaning multi-sensor data to alter the data and generate a clean signal. The clean signal can be recorded onto or otherwise stored on a memory (e.g., hard drive, flash drive, disk, or any other memory storage device) and/or transferred to other systems for additional processing or analysis.

An expected value of this invention to any system is first proportional to the signal-to-noise ratio; i.e. if there is little noise in the sensor measurements there is little value in removing it, conversely if the noise dominates the signal it is very valuable to efficiently extract it. Another value or improvement over the prior art lies in the automatic aspect of the invention. The number of Independent Components produced by ICA is (usually) the same as the number of channels measured. If this number if sufficiently large, inspection of all these components becomes infeasible and the value (i.e., improvement over existing technologies) of having an automated method is large. As can be appreciated, there are many commercial applications of such a system. Basically, the system and method described herein can be implemented in any application which relies on multi-channel sensor data to function and in which it is desirable to remove noise or artifact signals to generate a clean signal for further analysis. Prominent examples would be home and commercial EEG systems and multi-channel movement sensors systems. In such implementations, non-limiting examples of noise artifacts that can be removed include blink artifacts, eye movement, 60 Hz noise, bad channel artifacts, sweat artifacts, and head movement artifacts. Further details are provided below.

(3) Specific Details of Various Embodiments

Figure 3:
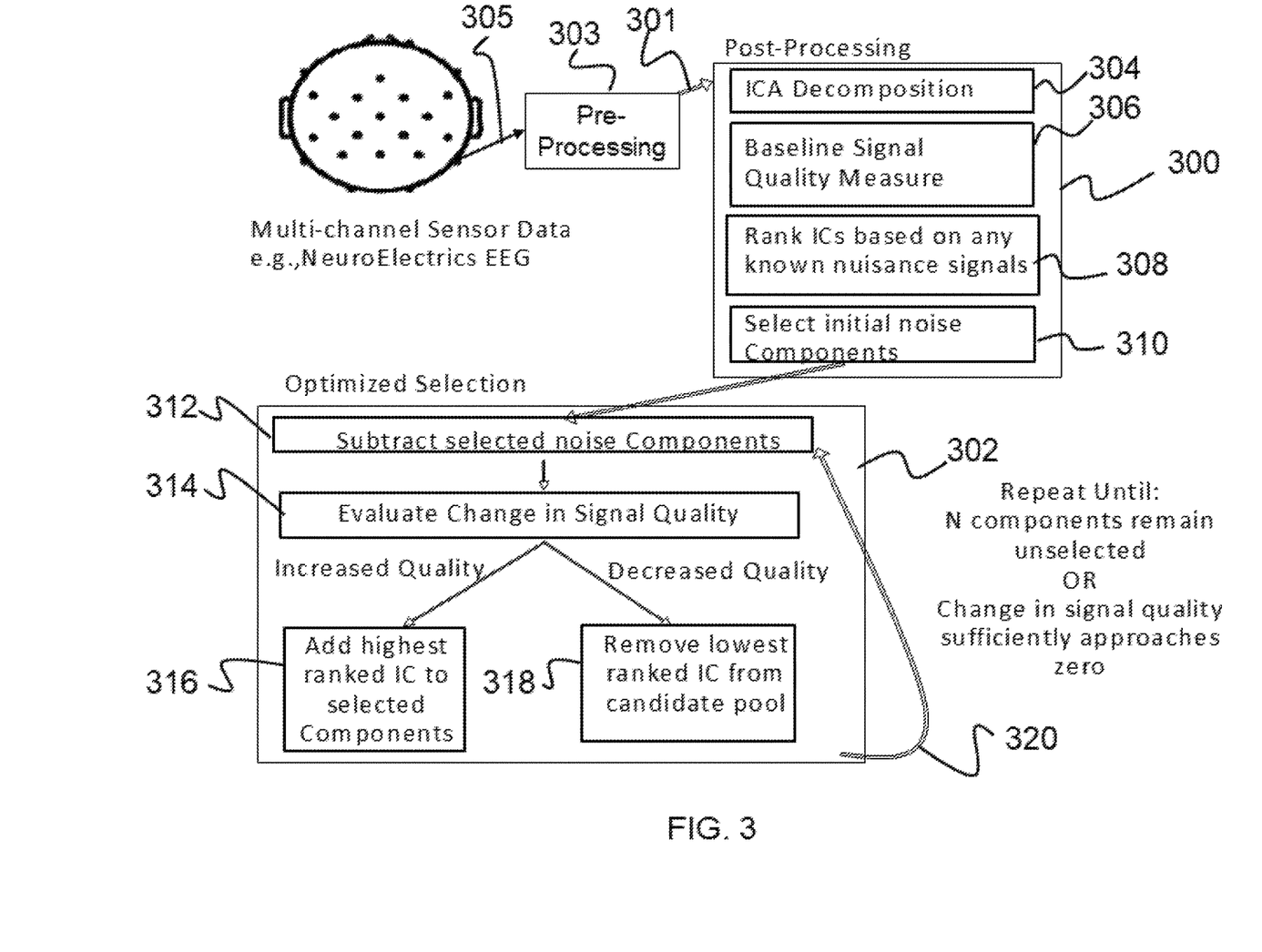
FIG. 3 is a schematic of information flow through the system according to various embodiments of the present invention, depicting sub-processes, and iterative selection of noise components.

As noted above, described is a system and method for automated artifact removal. In other words, the system operates to remove artifacts (e.g., signals associated with eye blinks, eye motions, head movement, EMGs and tDCS electrical interference, etc.) and output a clean signal (e.g., a clean electroencephalography (EEG) signal). As shown in FIG. 3, the system includes two major components, post processing 300 of pre-processed signals 301 and the optimized selection 302 of noise components for removal until the signal is of sufficient quality and designated a clean signal.

Desirably, a set of initial pre-processing 303 is done to improve signal quality from raw data 305 (e.g., EEG sensor data) before the independent component analysis (ICA) related post-processing 300. For example, first, any overtly bad channels in the raw data 305 are removed by comparing the frequency power spectrum calculated across the whole time series and z-scored across channels. Any channel that exceeds a z-score of two is removed from the data. The channels not identified as bad are re-referenced at every time point relative to the average across channels. Finally, each channel is filtered. As a non-limiting example, each channel is high-pass filtered at 0.1 Hz (or other predetermined band), and band-stop filtered between 59 and 61 Hz (or other predetermined range), resulting in a pre-processed signal 301.

Following the initial preprocessing 303, the independent component analysis decomposition 304 and baseline signal quality measurements 306 are made. Although not limited thereto, signal quality is assessed using a method derived from Daly et al. for EEG data, referred to as the Signal Quality Index (SQI). The Daly et al. reference can be found in a publication entitled, "What does clean EEG look like?", Conference proceedings: IEEE Engineering in Medicine and Biology Society Conference (2012), 3963-6, which is incorporated by reference as though fully set forth herein. Here, SQI is assessed using 1 second chunks of single channel EEG data which are labeled as either 0 for good or 1 for bad, based on various metrics derived by Daly et al. These values are then averaged together to get the SQI measure, which ranges from 0 to 1 where 0 corresponds to all samples marked as good and 1 as all samples marked as bad. The system of the present disclosure takes 100 randomly sampled 1 second chunks from the original data and averages the SQI across samples and channels to arrive at a single measure of quality. ICA decomposition 304 is done using any suitable technique, a non-limiting example of which includes using the pre-existing Matlab functions from the EEGLab package, specifically the default settings for the EEGLab implementation of the Logistic Info Max ICA algorithm. If there are known nuisance signals (e.g. accelerometer, electrooculargram, electrocardiogram, etc.) the Independent Components (ICs) can be ranked 308 as candidate noise components by their correlation with those nuisance signals, otherwise the components can be ranked in random order. The initial selection 310 of noise components can be done quantitatively if there exists known nuisance signals by setting a threshold on their correlation coefficients (e.g., independent components with r values greater than 0.5), and adding those independent components to the selected 'Noise Components' list. If no nuisance signals are known, the highest ranked independent component can be used to begin and is added to the Noise Components list.

After post-processing 300 is complete, the iterative optimized selection 302 process begins. First, the current set of selected Noise Components is removed 312 from the original pre-processed data 301 signal by subtracting each selected Noise Component from the pre-processed data 301. Then, the change in SQI is evaluated 314 such that the current SQI is compared against the SQI from the previous iteration, if this is the first iteration it is compared against the uncorrected signal. If the quality increases sufficiently, the next highest ranking IC is added 316 to the selected Noise Components list and the optimization processes proceeds 320 to the next iteration. If, instead, the quality decreases by a sufficient amount, the selected Noise Component with the lowest rank is removed 318 from the Noise Components list and it is ranked according to the amount of decrease in signal quality; here, the lowest ranking components correspond to the largest decrease in signal quality. The optimization process then proceeds 320 to the next iteration.

The process continues to proceed 320 to a next iteration, and continues in this iterative fashion until reaching a predetermined stopping condition. For example, the process repeats until any of the following stopping conditions are met: (1) all the ICs have at one time been a part of the Noise Component list, or (2) there exists a minimum N components not selected as noise.

In the above description, the "sufficiency" of quality increase required to add a selected component to the noise list was arbitrarily selected to be a decrease in SQI of –0.001 or more. This "sufficiency" value can be adapted to be more or less conservative depending on the reliability of the quality measure or the risk of removing non-nuisance signals. Similarly, the minimum 'N' number of non-noise components was arbitrarily selected to be 25% of the number of total components. This number can also be fit or modified given the risk aversion, signal type or quality of a particular dataset.

What is returned when this process completes is the optimally cleaned sensor data, and a set of ranked ICs where the highest ranked IC or ICs corresponds to noise components and the lowest ranked IC or ICs correspond to the signals of interest. The signal of interest or clean signal (e.g., clean EEG signal, etc.) is the resulting signal as desired for a number of processes. This clean signal can then be used in subsequent analyses, and the ranked components can be used to manually validate the optimization method if necessary. Finally, after noise component selection and removal is complete, the channels originally marked as bad are recreated by interpolating across spatially neighboring channels, returning a data set the same size as was input to the system with both known and unknown noise sources reduced or removed entirely.

Figure 6:
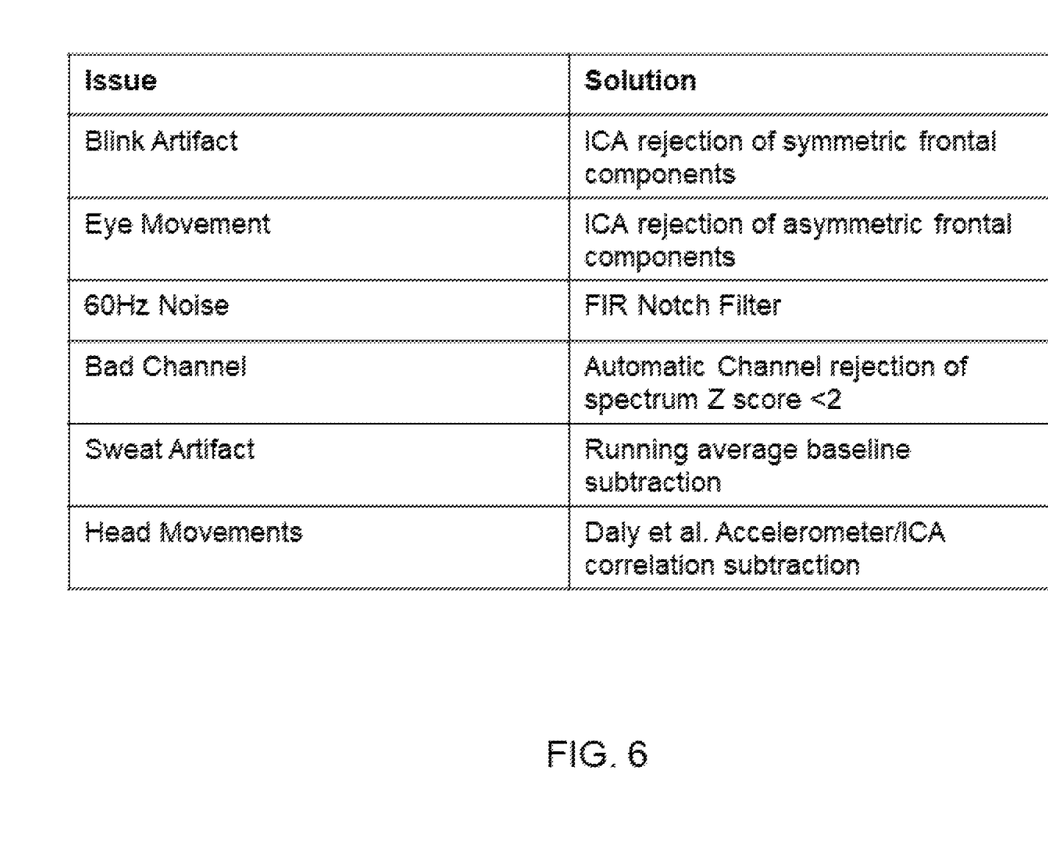
FIG. 6 is a table summarizing artifacts and example solutions to remove the artifact.

Although not limited thereto, the system as described herein was embodied in Matlab and executed on data collected on a 32 channel EEG data collection device, including an amplifier, electrodes and post-processing computer, commercially available as the Neuroelectrics EnoBio 32 as well as a similar prototype 64 channel device. The example version as implemented used EEGlab to import Neuroelectrics .easy EEG lab files directly fetched from an NEC box. The .easy files were converted into EEGlab data structures. Automatic channel rejection and DC offset removal were initially applied to all records. The system then executed the ICA which removed artifacts associated with eye blinks, eye motions, EMGs and tDCS electrical interference. To demonstrate the technological improvement over the prior art, the system was tested as an EEG pipeline with pilot data and the results have shown robust detection and removal of eye blink, eye movement, 60 Hz, bad channels, and sweat artifacts. FIG. 6 provides a table summarizing such artifacts and providing example solutions to remove the artifact, resulting in the clean signal.

Figure 4:
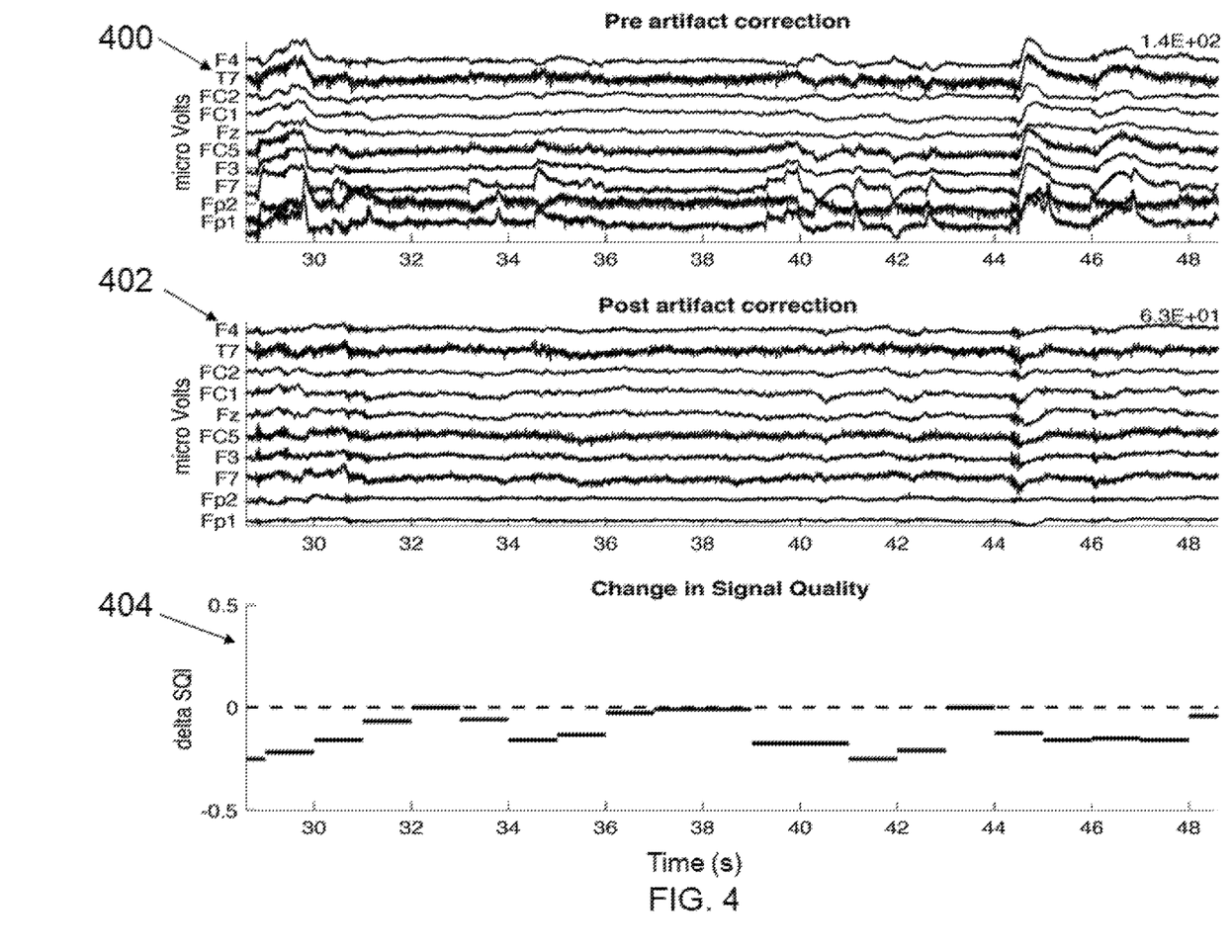
FIG. 4 depicts a time locked comparison of electroencephalography (EEG) data pre and post-artifact correction and corresponding change in the Signal Quality Index.
Figure 5:
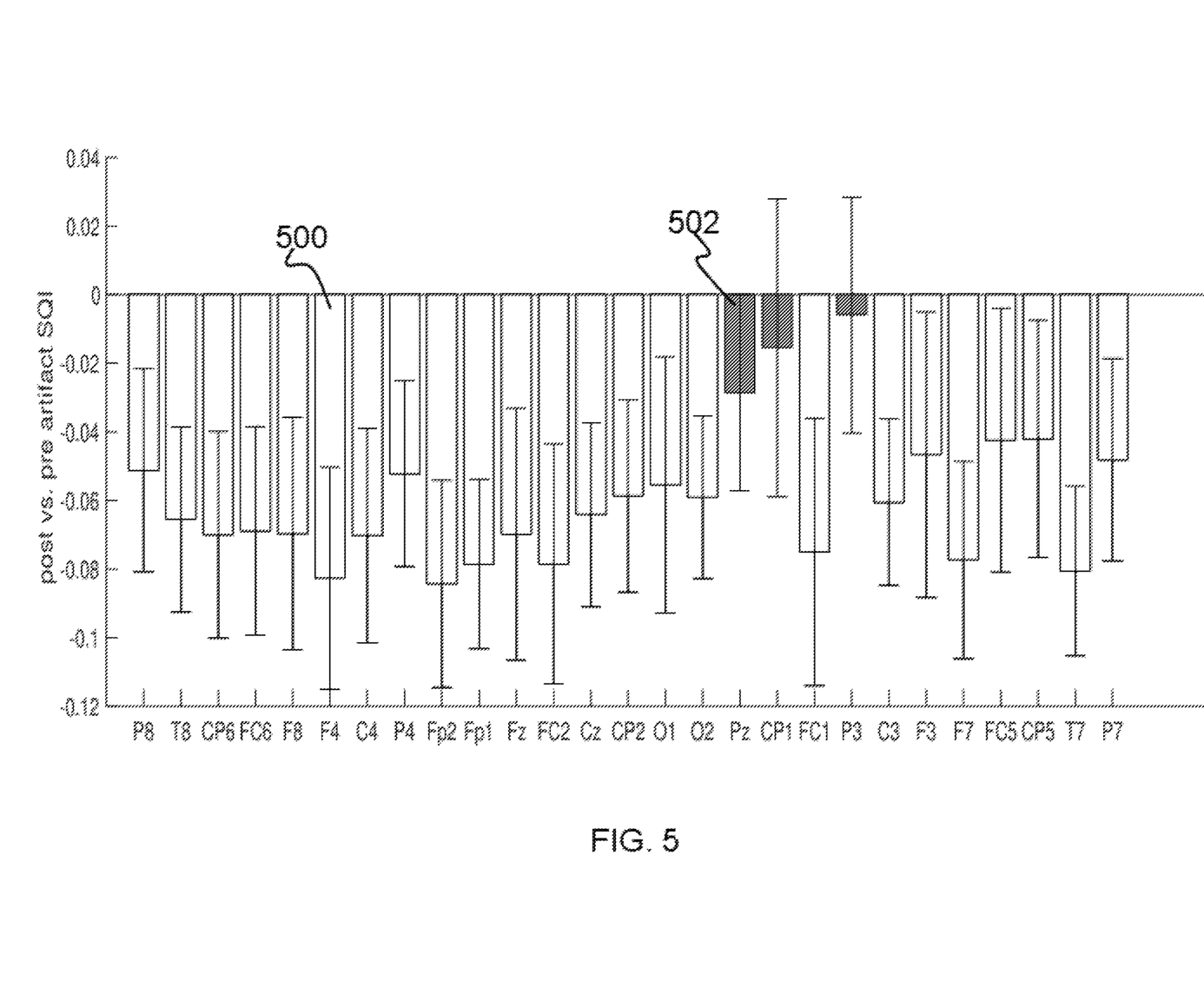
FIG. 5 is a bar graph depicting the average change in Signal Quality Index across sessions averaged within a given EEG channel.

The validation for this process was done in 50 separate sessions using a 32 channel EEG system along with nuisance signals acquired from a 3-channel accelerometer, 2-channel electrooculargram, and 1-channel electrocardiogram. FIG. 4 includes graphs depicting a time locked comparison of EEG data. Here a 20 sample of data for a sub-selection of 7 electrodes is shown with pre-artifact removal 400, and the time locked post-artifact removal 402. The peak-to-peak scale in micro Volts for each line plot is shown in the upper right-hand corner. The corresponding change in SQI (post artifact SQI minus pre-artifact SQI) 404 is shown on the bottom plot. The reductions in delta SQI correspond to improvements in the quality of the EEG signal. Quantitative results from these tests, shown in FIG. 5, illustrate that the average change in SQI decreased on all channels after running the automated artifact removal process, and significantly so in 23 out of 32 channels. Specifically, FIG. 5 is a graph illustrating the average change in Signal Quality Index across sessions averaged within a given EEG channel. Error bars show 95% confidence intervals. Solid white bars 500 show significant changes in SQI and grey bars 502 non-significant changes.

Finally, while this invention has been described in terms of several embodiments, one of ordinary skill in the art will readily recognize that the invention may have other applications in other environments. It should be noted that many embodiments and implementations are possible. Further, the following claims are in no way intended to limit the scope of the present invention to the specific embodiments described above. In addition, any recitation of "means for" is intended to evoke a means-plus-function reading of an element and a claim, whereas, any elements that do not specifically use the recitation "means for", are not intended to be read as means-plus-function elements, even if the claim otherwise includes the word "means". Further, while particular method steps have been recited in a particular order, the method steps may occur in any desired order and fall within the scope of the present invention.

What is claimed is:

1. A system for automated artifact removal to generate a clean signal, the system comprising:
   one or more processors and a memory, the memory being a non-transitory computer-readable medium having executable instructions encoded thereon, such that upon execution of the instructions, the one or more processors perform operations of:
   pre-processing a signal to generate a multi-channel, pre-processed signal;
   generating a plurality of independent components by performing independent component analysis decomposition on the multi-channel pre-processed signal;
   obtaining baseline signal quality measurements of the independent components based on a signal quality index (SQI);
   ranking the independent components based on known nuisance signals to generate a ranking of independent components from highest to lowest, otherwise ranking the independent components in random order;
   adding one or more independent components to a current noise components list according to the rankings derived from SOI changes upon removal
   generating a clean signal through optimized selection of the noise components based on a SQI and removal of independent components from the multi-channel, pre-processed signal, resulting in the clean signal; and
   recording the clean signal on a computer program product.

2. The system as set forth in claim 1, wherein generating the clean signal further comprises operations of:
removing the independent components that were added to the current noise components list from each channel in the multi-channel, pre-processed signal;
evaluating a change in signal quality by comparing a current signal quality index with a baseline signal quality or a signal quality index from a previous iteration;
if signal quality increases, adding a next highest ranking independent component in the ranking of independent components to the noise components list; and
if signal quality decreases, removing a lowest ranking independent component in the ranking of independent components from the noise components list.

3. The system as set forth in claim 2, wherein the process of generating the clean signal is repeated until a minimum number of independent components remain unselected or a change in signal quality is below a predetermined threshold.

4. The system as set forth in claim 1, wherein the process of generating the clean signal is repeated until a minimum number of independent components remain unselected or a change in signal quality is below a predetermined threshold.

5. A computer program product for automated artifact removal to generate a clean signal, the computer program product comprising:
a non-transitory computer-readable medium having executable instructions encoded thereon, such that upon execution of the instructions by one or more processors, the one or more processors perform operations of:
pre-processing a signal to generate a multi-channel, pre-processed signal;
generating a plurality of independent components by performing independent component analysis decomposition on the multi-channel pre-processed signal;
obtaining baseline signal quality measurements of the independent components based on a signal quality index (SQI):
ranking the independent components based on known nuisance signals to generate a ranking of independent components from highest to lowest, otherwise ranking the independent components in random order;
adding one or more independent components to a current noise components list according to the rankings derived from SQI changes upon removal
generating a clean signal through optimized selection of the noise components based on a SQI and removal of independent components from the multi-channel, pre-processed signal, resulting in the clean signal; and
recording the clean signal on a computer program product.

6. The computer program product as set forth in claim 5, wherein generating the clean signal further comprises operations of:
removing the independent components that were added to the current noise components list from each channel in the multi-channel, pre-processed signal;
evaluating a change in signal quality by comparing a current signal quality index with a baseline signal quality or a signal quality index from a previous iteration;
if signal quality increases, adding a next highest ranking independent component in the ranking of independent components to the noise components list; and
if signal quality decreases, removing a lowest ranking independent component in the ranking of independent components from the noise components list.

7. The computer program product as set forth in claim 6, wherein the process of generating the clean signal is repeated until a minimum number of independent components remain unselected or a change in signal quality is below a predetermined threshold.

8. The computer program product as set forth in claim 5, wherein the process of generating the clean signal is repeated until a minimum number of independent components remain unselected or a change in signal quality is below a predetermined threshold.

9. A computer implemented method for automated artifact removal to generate a clean signal, the method comprising an act of:
causing one or more processors to execute instructions encoded on a non-transitory computer-readable medium, such that upon execution, the one or more processors perform operations of:
pre-processing a signal to generate a multi-channel, pre-processed signal;
generating a plurality of independent components by performing independent component analysis decomposition on the multi-channel pre-processed signal:
obtaining baseline signal quality measurements of the independent components based on a signal quality index (SQI);
ranking the independent components based on known nuisance signals to generate a ranking of independent components from highest to lowest, otherwise ranking the independent components in random order;
adding one or more independent components to a current noise components list according to the rankings derived from SQI changes upon removal
generating a clean signal through optimized selection of the noise components based on a SQI and removal of independent components from the multi-channel, pre-processed signal, resulting in the clean signal; and
recording the clean signal on a computer program product.

10. The method as set forth in claim 9, wherein generating the clean signal further comprises operations of:
removing the independent components that were added to the current noise components list from each channel in the multi-channel, pre-processed signal;
evaluating a change in signal quality by comparing a current signal quality index with a baseline signal quality or a signal quality index from a previous iteration;
if signal quality increases, adding a next highest ranking independent component in the ranking of independent components to the noise components list; and
if signal quality decreases, removing a lowest ranking independent component in the ranking of independent components from the noise components list.

11. The method as set forth in claim 10, wherein the process of generating the clean signal is repeated until a minimum number of independent components remain unselected or a change in signal quality is below a predetermined threshold.

12. The method as set forth in claim 9, wherein the process of generating the clean signal is repeated until a minimum number of independent components remain unselected or a change in signal quality is below a predetermined threshold.

* * * * *